United States Patent
Yao et al.

(10) Patent No.: US 11,006,684 B2
(45) Date of Patent: *May 18, 2021

(54) GLIDE-ON COATING FOR POLYMERIC GLOVES

(71) Applicant: Medline Industries, Inc., Northfield, IL (US)

(72) Inventors: Min Yao, Libertyville, IL (US); Yuli Wu, Shijiazhuange (CN); Jaxon Dai, Shanghai (CN); Komal Pokharel-Adhikari, Mundelein, IL (US); Guixi Liu, Shijiazhuang (CN)

(73) Assignee: Medline Industries, Inc., Northfield, IL (US)

( * ) Notice: Subject to any disclaimer, the term of this patent is extended or adjusted under 35 U.S.C. 154(b) by 40 days.

This patent is subject to a terminal disclaimer.

(21) Appl. No.: 16/568,353

(22) Filed: Sep. 12, 2019

(65) Prior Publication Data
US 2020/0000159 A1    Jan. 2, 2020

Related U.S. Application Data

(63) Continuation of application No. 15/597,298, filed on May 17, 2017, now Pat. No. 10,448,686.

(Continued)

(51) Int. Cl.
| | | |
|---|---|---|
| *A41D 19/015* | (2006.01) | |
| *A41D 19/00* | (2006.01) | |
| *A61L 31/04* | (2006.01) | |
| *C08J 7/04* | (2020.01) | |
| *A61B 42/10* | (2016.01) | |

(Continued)

(52) U.S. Cl.
CPC ..... *A41D 19/0082* (2013.01); *A41D 19/0062* (2013.01); *A61B 42/10* (2016.02); *A61L 31/04* (2013.01); *A61L 31/048* (2013.01); *A61L 31/10* (2013.01); *A61L 31/14* (2013.01); *C08J 7/0427* (2020.01); *C09D 5/00* (2013.01); *C09D 7/20* (2018.01); *C09D 7/45* (2018.01); *C09D 7/61* (2018.01); *C09D 175/04* (2013.01); *A41D 2400/44* (2013.01); *A41D 2500/54* (2013.01); *A61L 2400/10* (2013.01); *C08J 2327/06* (2013.01); *C08J 2475/04* (2013.01); *C08J 2483/04* (2013.01)

(58) Field of Classification Search
CPC ............ A41D 19/0058; A41D 2400/44; A41D 19/0055; A41D 19/0082; A61B 42/00; A61B 42/10
See application file for complete search history.

(56) References Cited

U.S. PATENT DOCUMENTS

| | | | | |
|---|---|---|---|---|
| 6,016,570 A | * | 1/2000 | Vande Pol | A41D 19/0058 2/161.7 |
| 6,709,725 B1 | * | 3/2004 | Lai | A41D 19/0058 2/168 |
| 7,776,368 B2 | * | 8/2010 | Hamann | A41D 19/0058 424/744 |
| 10,448,686 B2 | * | 10/2019 | Yao | A61L 31/048 |

(Continued)

*Primary Examiner* — Robert H Muromoto, Jr.
(74) *Attorney, Agent, or Firm* — Fitch, Even, Tabin & Flannery, L.L.P.

(57) ABSTRACT

Polymeric gloves include a donning-facilitating coating. The donning-facilitating coating facilitates a hand of a user to glide into and out of the glove while either leaving a visible residue on the hand of the user, or not leaving a visible residue on the hand of the user, when the donning-facilitating coating is contacted by the hand of the user.

15 Claims, 3 Drawing Sheets

Related U.S. Application Data

(60) Provisional application No. 62/399,064, filed on Sep. 23, 2016.

(51) Int. Cl.
  *C09D 7/61* (2018.01)
  *C09D 7/20* (2018.01)
  *C09D 7/45* (2018.01)
  *A61L 31/10* (2006.01)
  *A61L 31/14* (2006.01)
  *C09D 5/00* (2006.01)
  *C09D 175/04* (2006.01)
  *A41D 27/00* (2006.01)

(56) References Cited

U.S. PATENT DOCUMENTS

| | | | |
|---|---|---|---|
| 2001/0053421 A1* | 12/2001 | Schaller | A41D 19/0058 427/557 |
| 2002/0015812 A1* | 2/2002 | Littleton | A61B 42/00 428/36.8 |
| 2003/0115659 A1* | 6/2003 | Williams | B29D 99/0067 2/161.7 |
| 2003/0118837 A1* | 6/2003 | Modha | A41D 19/0058 427/557 |
| 2005/0044609 A1* | 3/2005 | Vistins | B29D 99/0067 2/161.7 |
| 2005/0182156 A1* | 8/2005 | Liu | A61B 42/00 428/36.8 |
| 2006/0059604 A1* | 3/2006 | Lai | B29C 41/14 2/168 |
| 2006/0068138 A1* | 3/2006 | Janssen | A41D 19/0058 2/159 |

* cited by examiner

GLIDE-ON COATING FOR POLYMERIC GLOVES

FIELD

This disclosure relates to coatings for polymeric gloves and, and in some embodiments, to donning-facilitating coatings for polymeric gloves.

BACKGROUND

Generally, medical gloves are made of many conventional materials, such as latex, nitrile, and polyvinyl chloride (PVC). However, when hands are wet or damp, as when a user (e.g., surgeon or laboratory worker) attempts to put on the gloves after washing his or her hands or applying a disinfectant solution, foam, or gel to his or her hands, the gloves can be quite difficult to put on due to friction between the interior of the glove and wet or damp skin. This can often result in the gloves ripping during donning. It would be desirable to provide a glove that is suitable for use with disinfectant solutions.

When using gloves, it is often important to follow facility cleanliness procedures after doffing the gloves. In some cases, it may be useful to provide a glove that provides a visual reminder that the user should follow the cleanliness procedures.

FIGURES

DETAILED DESCRIPTION

Generally, donning-facilitating coating compositions for polymeric gloves, polymeric gloves including such compositions, and associated methods of making such compositions and gloves are described herein.

Figure 1:
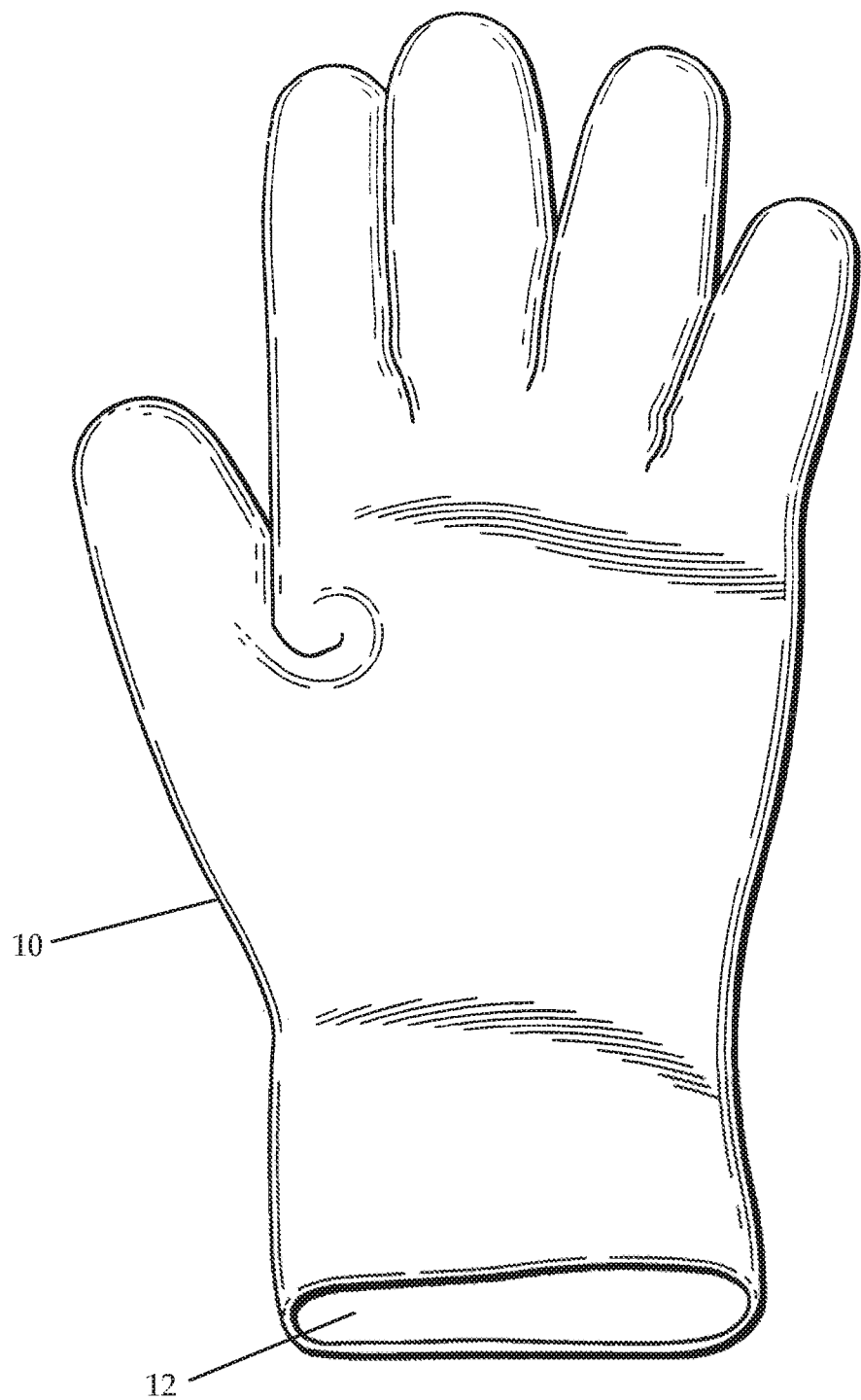
FIG. 1 illustrates an exemplary glove prepared in accordance with the present teachings.
Figure 2:
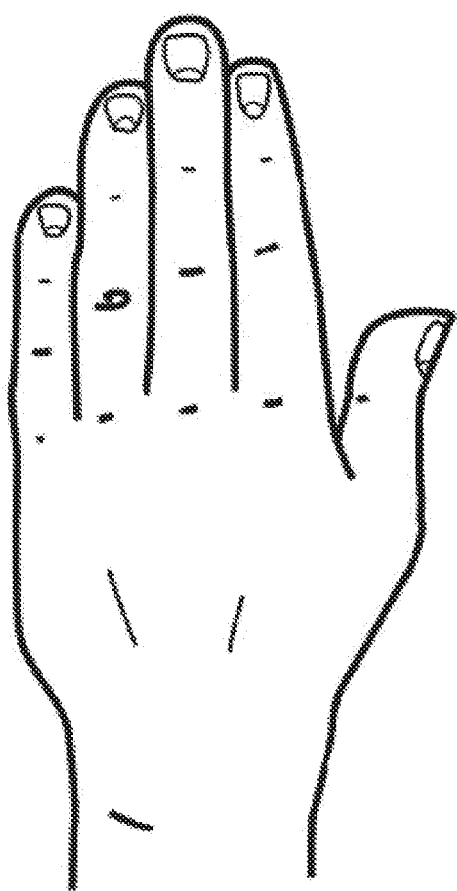
FIG. 2 illustrates a user's hand before donning the exemplary glove shown in FIG. 1.
Figure 3:
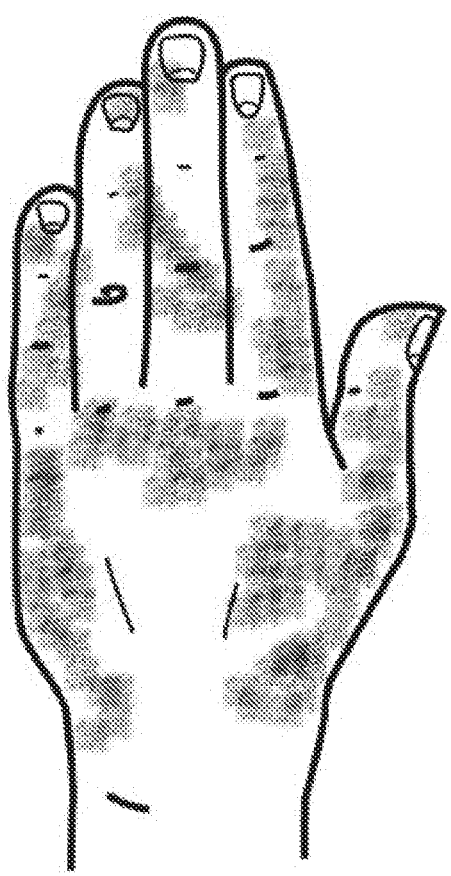
FIG. 3 illustrates the user's hand after doffing the exemplary glove shown in FIG. 1.

In one embodiment, an interior surface (i.e., the hand-contacting surface) of a polymeric glove (e.g., a polyvinyl chloride glove) includes a donning-facilitating coating that facilitates a hand of a user to glide into the interior of the glove and out of the interior of the glove. The coating may leave colored visible residue on the hand of the user when the hand of the user, which had an alcohol-based disinfectant thereon, is removed from the glove. As depicted in FIG. 1, for instance, the glove 10 may have a coating 12 on the interior surface thereof. When the user has donned and subsequently doffed the glove, the user's hand is left with a colored indicia, as seen in FIGS. 2 and 3.

In another embodiment, an interior surface of a glove includes a donning-facilitating coating that facilitates a hand of a user to glide into the interior of the glove and out of the interior of the glove, the coating including a modifier that enhances adhesion of the coating to the glove material. The coating may be formulated such that substantially no visible residue is left on the hand of the user when the donning-facilitating coating is contacted by the hand of the user having an alcohol-based disinfectant thereon.

The polymeric gloves described herein may be made of conventional materials, and the present disclosure especially contemplates in some embodiments gloves made of a polyvinyl chloride material. Such gloves are prepared from glove formulations as is conventional.

In some aspects, the polymeric glove formulation includes one or more polyvinyl chloride resins. The polymeric glove formulation may include from about 20 to about 40 parts of a first polyvinyl chloride resin and from about 60 to about 80 parts of a second polyvinyl chloride resin distinct from the first polyvinyl chloride resin. Exemplary suitable polyvinyl chloride resins include but are not limited to LP170G resin (manufactured by LG Chemicals, South Korea), PR-F resin (manufactured by Formosa Plastics, Taiwan), PSH 30 resin (manufactured by Shenyang Chemical Co. Ltd., People's Republic of China (PRC)), or the like, or combinations thereof. While some of the polymeric glove formulations described herein include two distinct polyvinyl chloride resins, it will be appreciated that only one polyvinyl chloride resin can be used instead. Generally, two polyvinyl chloride resins can be mixed with each other in various proportions.

The glove may be formulated with other conventional components, such as a one or more plasticizers, viscosity reducers, stabilizers, and combinations thereof. For example, in some embodiments, the polymeric glove formulation glove includes from about 76 to about 82 parts of a plasticizer. In one aspect, the plasticizer includes, but is not limited to a phthalate compound. Suitable phthalate compounds include but are not limited to diisononyl phthalate (DINP) (manufactured by LG Chemicals, South Korea), dioctyl terephthalate (DOTP), manufactured by Exxon Mobil, Singapore, or the like, or combinations thereof. Other suitable plasticizes include such as epoxidized soybean oil (ESBO), 1,2-cyclohexane dicarboxylic acid diisononyl ester (DINCH), dioctyl phthalate (DOP), dibutyl phthalate (DBP), diisooctyl phthalate (DIOP), di-2-ethylhexyl adipate (DOA), tris(2-ethylhexyl)trimellitate (TOTM), epoxidized soybean oil (ESO), expandable polystyrene (EPS), diethylene glycol dibenzoate (DEDB), dipropylene glycol dibenzoate (DPGDB), acetyl tributyl citrate (ATBC), tributyl citrate (TBC). Any other suitable plasticizer may be employed.

The polymeric glove formulation may include from about 10 to about 15 parts of a viscosity reducer. Suitable viscosity reducers include 2,2,4-Trimethyl-1,3-pentanediol diisobutyrate (TXIB), n-alkane type viscosity reducers such as D70, D80, D90, and D100, or the like. In some embodiments, the polymeric glove formulation includes from about 0.5 to about 0.8 parts of a stabilizer. Suitable stabilizers include calcium stearate, zinc stearate, or the like, or combinations thereof.

To provide lubrication, the interior of the glove may be coated with a coating composition. Any suitable coating composition may be employed. In some embodiments, the coating composition includes a polyurethane resin-containing solution and water. In some aspects, the polyurethane resin-containing solution includes polyurethane resin, silicon dioxide (i.e., silica), a surfactant, and water. A polyurethane resin-containing solution according to some embodiments includes from about 20 to about 60 wt. % polyurethane resin, from about 1 to about 10 wt. % silicon dioxide, from about 0.1 to about 2 wt. % surfactant, and from about 28 to about 79 wt. % water. The silicon dioxide may comprise particles sized from about 0.01 micron to about 0.2 micron. Suitable surfactants may be nonionic surfactants including but not limited to polysiloxane or the like.

In one embodiment, the coating composition includes about 1 part polyurethane resin-containing solution, from about 20 to about 25 parts water, and an optional colorant, such as from about 0.1 to about 10 parts colorant. Without wishing to be limited by theory, the polyurethane resin-containing solution provides a donning-facilitating coating for the interior of the polymeric glove and permits a user having a wet or damp hand having an alcohol-based disinfectant thereon to smoothly insert the hand into the glove, and to smoothly remove the hand from the glove without the hand sticking to the interior surface of the glove, which would normally enhance the risk of the glove ripping. The colorant may be a food-grade dye or other colorant that is suitable to leave a visible residue on the hands of the user when the hands of the user, prior to being inserted into the glove, contain wetness provided by an alcohol-based disinfectant. This visible residue can later be washed off the hand of the user via water and/or water and soap combination.

Without wishing to be limited by theory, when a hand of a user that is wet or damp with an alcohol-based disinfectant is inserted into the glove and comes into contact with the interior surface of the glove and the donning-facilitating coating (which includes the colorant) on the interior surface, the alcohol (e.g., ethanol, isopropyl alcohol, or the like) causes the colorant to be released from the donning-facilitating coating and come in contact to and stick to the wet hands of the user due to the wetness provided by the presence of alcohol thereon. The visible residue left on the hands of the user by the release of the colorant from the donning-facilitating coating advantageously reminds the user to wash his or her hands promptly after taking the glove off.

Accordingly, in one aspect, one embodiment of the present invention includes a donning-facilitating composition for coating an interior surface of a polymeric glove, which, when coated onto the interior surface of the glove, is configured to facilitate a hand of a user to glide into and out of the glove, and which comprises a polyurethane resin-containing solution and a colorant configured to leave a visible residue on the hand of the user when the interior surface of the glove having the donning-facilitating coating is contacted by the hand of the user having an alcohol-based disinfectant thereon.

In some aspects, a donning-facilitating composition for coating an interior surface of a polymeric glove includes a polyurethane resin-containing solution and silicon oxide (i.e., silica particles) which, after coming into contact with an alcohol typically present in hand disinfectants and cleaning gels, becomes unstable such that the silica particles start to agglomerate, and the combination of the unstable polyurethane resin-containing solution and the agglomerated silica particles form a visible powdery reside on the user's hand.

In another embodiment, an interior surface (i.e., the hand-contacting surface) of a polymeric glove includes a donning-facilitating coating that facilitates a hand of a user to glide into the interior of the glove and out of the interior of the glove, and that leaves no visible residue on the hand of the user when the hand of the user, which was inserted into the glove while having an alcohol-based disinfectant thereon, is removed from the glove. The polymeric glove according to this embodiment includes substantially identical ingredients and otherwise is substantially similar to the polymeric glove according to the colorant-including embodiment.

The glove formulation according to this embodiment need not include a colorant, but instead includes a modifier configured to retain the polyurethane resin-containing solution of the donning-facilitating coating on the interior surface of the glove such that substantially no visible residue is left on the hand of the user when the donning-facilitating coating is contacted by a hand of the user having an alcohol-based disinfectant thereon.

Some modifiers suitable for retaining the polyurethane resin-containing solution of the donning facilitating coating on the interior surface of the glove even when the hand of the user coming into contact with the interior surface of the glove is wetted with an alcohol-containing disinfectant may include but are not limited to: wax, shellac, polyurethane, polyurethane and wax mixture, polyethylene glycol, polyethylene emulsion, polyvinyl acetate, hyaluronic acid, or the like, or combinations thereof. Preferably, the modifier is an anionic polyacrylamide having a molecular weight greater than 14,000,000. It has been found that the use of such a modifier can be effective to provide a glove coating composition that leaves little or no residue on the hands upon doffing the glove. Other polyacrylamides, as well as polyacrylates or hydroxyethyl methacrylate, may be employed as the modifier.

In one form, the modifier is an anionic polyacrylamide having a molecular weight of at least about 10,000,000, preferably at least about 11,000,000, and more preferably at least about 14,000,000. In some embodiments, the glove formulation, which includes the donning-facilitating polyurethane resin-containing solution as in above-described embodiment including the colorant, includes about 1 part polyurethane resin-containing solution, from about 20 to about 25 parts water, and about 0.001 to about 0.01 parts modifier. In one embodiment, the glove formulation includes about 1 part polyurethane resin-containing solution, about 25 parts water, and about 0.006 parts modifier.

The donning-facilitating coating, which was described above, permits a user having a wet or damp hand covered with a residue of an alcohol-based disinfectant, to smoothly insert the hand into the polymeric glove, and to smoothly remove the hand from the polymeric glove without the hand sticking to the interior surface of the glove, which would normally enhance the risk of the glove ripping. Without wishing to be limited by theory, the modifier retains most if not all of the polyurethane resin-containing solution (which contains silicon dioxide particles as described above) of the donning facilitating coating on the interior surface of the polymeric glove even when the hand of the user coming into contact with the interior surface of the glove is wetted with an alcohol-containing disinfectant. In other words, the modifier acts as a crosslinking, adhesion, and/or bonding agent that facilitates a stronger bond between the donning-facilitating polyurethane resin-containing solution and the polymer (e.g., polyvinyl chloride) based interior surface of the polymeric glove, thereby advantageously permitting a user having a wet or damp hand covered with a residue of an alcohol-based disinfectant to smoothly insert the hand into the glove, and to smoothly remove the hand from the glove without the hand sticking to the interior surface of the glove, and such that substantially no visible residue is left on the hand of the user.

Accordingly, in one aspect, one embodiment of the present invention includes a donning-facilitating composition for coating an interior surface of a polymeric glove, which, when coated onto the interior surface of the glove, is configured to facilitate a hand of a user to glide into and out of the glove, and which comprises a polyurethane resin-containing solution and a modifier configured to retain the polyurethane resin-containing solution on the interior surface of the glove such that no visible residue is left on the hand of the user when the donning-facilitating composition is contacted by the hand of the user having an alcohol-based disinfectant thereon.

The gloves may be formed by creating a plastisol of the glove base material and dipping the plastisol on a form into the polyurethane resin. The dipped glove then may be dried. Generally, the drying temperature can depend on the temperature of the enclosure where the gloves are made. In particular, in some aspects, when the gloves are manufactured at a temperature from −10° C. to 0° C., the drying (i.e., curing) temperature can be from 150° C. to 165° C., when the gloves are manufactured at a temperature from 0° C. to 10° C., the drying (i.e., curing) temperature can be from 130° C. to 150° C., when the gloves are manufactured at a temperature from 10° C. to 20° C., the drying (i.e., curing) temperature can be from 120° C. to 130° C., when the gloves are manufactured at a temperature from 20° C. to 30° C., the drying (i.e., curing) temperature can be from 100° C. to 120° C., and when the gloves are manufactured at a temperature from 30° C. to 40° C., the drying (i.e., curing) temperature can be from 80° C. to 100° C.

Advantages and embodiments of the elastomeric polymeric gloves as described herein are further illustrated by the following examples; however, the particular conditions, processing schemes, materials, and amounts thereof recited in these examples, as well as other conditions and details, should not be construed to unduly limit the compositions and methods described herein.

Example 1

Polymeric gloves were made using a known process for making gloves. Generally, the glove formulation and resin components included: 20-40 parts PVC A-LP170G resin (purchased from LG Chemicals, South Korea); 60-80 parts PVC B-PR-F resin (purchased from Formosa Plastics, Taiwan) or PSH 30 resin (purchased from Shenyang Chemical Co. Ltd., PRC); 76-82 parts plasticizer DINP, purchased from LG Chemicals, South Korea, or DOTP, purchased from Exxon Mobil, Singapore; 10-12 parts viscosity reducer TXIB, purchased from Eastman Chemicals, PRC); 0.5-0.8 parts stabilizer SBA-203CZ-G, purchased from Fa'aihong Chemical, PRC; 1 part polyurethane resin-containing solution A-112, purchased from Jija, Taiwan, and 25 parts water.

The polyurethane resin-containing solution A-112 had the following composition:

TABLE 1

| Chemicals | CAS Number | % |
| --- | --- | --- |
| polyurethane resin | 71394-21-3 | 20-60 |
| Silica | 14464-46-1 | 1-10 |
| Surfactant | 125997-17-3 | 0.1-2 |
| Water | 7732-17-3 | balance |

The polymeric gloves were prepared as follows. The modifier-containing solution was mixed with water for about 1-1.5 hours while stirring continuously. After that, the polyurethane resin-containing solution was stirred continuously for another 45-60 minutes to provide a uniform, homogeneous solution. The temperature of the polyurethane resin-containing solution was maintained at 50-60° C. during the stirring.

Plastisol (e.g., mixture of at least one polyvinyl chloride resin, plasticizer, viscosity reducer, stabilizer, and colorant) was provided in a tank at a temperature of from about 60° C. to about 65° C. The clean hand former was dipped for 15 seconds in the plastisol tank and released for trickling, and then dried for 6 minutes at about 200-230° C. followed by cooling to about 110-120° C. The temperature of the polyurethane resin-containing solution was at about 50-60° C. in the other tank at a pH of about 7.5 to about 9.5. The viscosity of the polyurethane resin-containing solution was 2-6 centipoise (cps).

When the temperature of the hand former with glove was at about 110° C. to about 120° C., the plastisol was dipped in the polyurethane resin-containing solution for 15 seconds, released and dried for 2 minutes. The drying temperature was from about 80° C. to about 165° C. The speed of the line was 140-180 samples/minute. The water evaporated off completely from the former and after cooling, the gloves were rolled out in inverted fashion such that the polyurethane coating was on the inside of the glove.

Treated gloves were then tested for tensile properties according to ASTM D412. The easy donning evaluation was as follows: Grade 1: tacky; worst donning experience; Grade 2: tough surface; not good donning experience; Grade 3: smooth surface; normal donning experience; Grade 4: very smooth surface; good donning experience; Grade 5: excellent smoothness; best donning experience; Dry hand donning: hands are not washed or disinfected; Wet hand donning: hands are washed with water and/or disinfected with alcohol solution or gel. The results were compared to a commercial coating.

The results were as follows:

TABLE 2

| | Example 1 | Commercial coating |
| --- | --- | --- |
| Tensile at Break | 8.5 kN/m | 8.8 kN/m |
| Elongation at Break | 330% | 340% |
| Easy donning grade (dry) | 5 | 4 |
| Easy donning grade (wet) | 5 | 1 |
| Easy donning grade (alcohol) | 5 with lots white powder residue | 2 with slight white powder residue |

Example 2

Example 1 is repeated, but in addition 0.1 part of a food colorant is added to the polyurethane solution.

Example 3

Example 2 is repeated, but instead of 0.1 part of food colorant, 10 parts of food colorant are added to the polyurethane solution.

Example 4

PVC gloves and polyurethane resin-containing solution were made as described in example 1, but 0.006 parts of an anionic polyacrylamide with a molecular weight of at least 14,000,000 was added to the polyurethane solution. In other words, the glove formulation included: 20-40 parts PVC A-LP170G resin (purchased from LG Chemicals, South Korea); 60-80 parts PVC B-PR-F resin (purchased from Formosa Plastics, Taiwan) or PSH 30 resin (purchased from Shenyang Chemical Co. Ltd., PRC); 76-82 parts plasticizer DINP, purchased from LG Chemicals, South Korea, or DOTP, purchased from Exxon Mobil, Singapore; 10-12 parts viscosity reducer TXIB, purchased from Eastman Chemicals, PRC; 0.5-0.8 parts stabilizer SBA-203CZ-G, purchased from Fa'aihong Chemical, PRC; 0.006 parts of an anionic polyacrylamide with a molecular weight of at least 14,000,000, 1 part polyurethane resin-containing solution A-112, purchased from Jija, Taiwan, and 25 parts water.

The conditions of the line were as follows:

TABLE 3

| Check Item | Inner quality standard regular PVC glove | Inner quality standard regular PVC glove | Result |
| --- | --- | --- | --- |
| Line speed: Sample/min | 128-135 | 123-130 | More than 5/min |
| PU drying temp | 125-135 | 135-145 | Higher than 10 degree |
| tension: Mpa | 15.9-18.3 | 15.8-18.2 | Same |
| elongation: % | 380-430 | 385-438 | Almost same |
| Color | Natural | Natural | Same |

Treated gloves were then tested for tensile properties according to ASTM D412.

Results were as follows: Average load at break: >8 kN/m—Passed ASTM standard. Average elongation at break: >300%-Passed ASTM standard.

The directions for the Damp Don Performance test conducted were as follows:
1. In a big plastic tub, fill in the tap water such that both hands are completely immersed in water for 5 secs.
2. Place two pieces of filter paper on the desk in a dry place.
3. After soaking the hand in water, put the two palms facing down on the filter paper and pat down on the tissue 3 times.
4. Then turn the hands upside down and pat down for three times again
5. Repeat the process with every two new tissue papers performing steps 3 and 4.
6. Don the gloves one glove at a time. When one hand has a glove, put another glove using the gloved hand.

Medline industries alcohol gel Skintegrity Instant Hand Sanitizers (Conc. 63% ethanol) was used as the alcohol-based disinfectant. About 20-25 g gel alcohol was used for one test.

The hands were rubbed with gel alcohol and the gloves were donned. The gloves were easy to don and no residue was left. Measurement of tack on the gloves: Grade 1: tacky; worst donning experience; Grade 2: tough surface; not good donning experience; Grade 3: smooth surface; normal donning experience; Grade 4: very smooth surface; good donning experience; Grade 5: excellent smoothness; best donning experience; Dry hand donning: hands are not washed or disinfected; Wet hand donning: hands are washed with water and/or disinfected with alcohol solution or gel.

Results were as follows:

TABLE 4

| | Example 4 | Normal coating |
| --- | --- | --- |
| Easy donning grade (dry) | 5 | 4 |
| Easy donning grade (wet) | 5 | 1 |
| Easy donning grade (alcohol) | 5 with no powder residue | 2 with slight white powder residue |

The foregoing descriptions are not intended to represent the only forms of easy to put on elastomeric gloves in regard to the details of the formulation. Changes in form and in proportion of parts, as well as the substitution of equivalents, are contemplated as circumstances may suggest or render expedient. Similarly, while the elastomeric gloves and methods of making thereof have been described herein in conjunction with specific embodiments, many alternatives, modifications, and variations will be apparent to those skilled in the art in light of the foregoing description.

The invention claimed is:

1. A polymeric glove having an interior surface for contacting a hand of a user, the interior surface including a donning-facilitating coating configured to facilitate a hand of a user to glide into and out of the glove, the donning-facilitating coating comprising a polyurethane resin-containing solution and a colorant configured to leave a visible residue on the hand of the user when the donning-facilitating coating is contacted by the hand of the user having an alcohol-based disinfectant thereon, wherein the polyurethane resin-containing solution includes 20-60 wt. % polyurethane resin, 1-10 wt. % silicon dioxide, 0.1-2 wt. % nonionic surfactant comprising a polysiloxane, and 28-79 wt. % water.

2. The glove of claim 1, wherein the polymeric glove is a polyvinyl chloride glove.

3. The glove of claim 1, further comprising 20-40 parts of a first polyvinyl chloride resin and 60-80 parts of a second polyvinyl chloride resin distinct from the first polyvinyl chloride resin.

4. The glove of claim 1, further comprising: 76-82 parts of a plasticizer,
10-15 parts of a viscosity reducer,
and 0.5-0.8 parts of a stabilizer.

5. The glove of claim 1, wherein the silicon dioxide comprises particles sized from 0.01 micron to 0.2 micron.

6. A polymeric glove having an interior surface for contacting a hand of a user, the interior surface including a donning-facilitating coating configured to facilitate a hand of a user to glide into and out of the glove, the donning-facilitating coating comprising a polyurethane resin-containing solution and a modifier configured to retain the polyurethane resin-containing solution on the interior surface of the glove when the donning-facilitating coating is contacted by the hand of the user having an alcohol-based disinfectant thereon, wherein the polyurethane resin-containing solution includes 20-60 wt. % polyurethane resin, 1-10 wt. % silicon dioxide, 0.1-2 wt. % nonionic surfactant comprising a polysiloxane, and 28-79 wt. % water.

7. The glove of claim 6, wherein the polymeric glove is a polyvinyl chloride glove.

8. The glove of claim 6, further comprising 20-40 parts of a first polyvinyl chloride resin and 60-80 parts of a second polyvinyl chloride resin distinct from the first polyvinyl chloride resin.

9. The glove of claim 6, further comprising: 76-82 parts of a plasticizer, 10-15 parts of a viscosity reducer, and 0.5-0.8 parts of a stabilizer.

10. The glove of claim 6, wherein the silicon dioxide comprises particles sized from 0.01 micron to 0.2 micron.

11. The glove of claim 6, wherein the modifier is an anionic polyacrylamide with a molecular weight of at least 14,000,000.

12. The glove of claim 6, wherein the donning-facilitating coating is applied by dipping the interior surface of the glove.

13. A polymeric glove having an interior surface for contacting a hand of a user, the interior surface including a donning-facilitating coating configured to facilitate a hand of a user to glide into and out of the glove, the donning-facilitating coating comprising a polyurethane resin and silicon dioxide configured to agglomerate and form a visible residue on the hand of the user having an alcohol-based disinfectant thereon, wherein the donning-facilitating coating comprises 20-60 wt. % of the polyurethane resin, 1-10 wt. % of the silicon dioxide, 0.1-2 wt. % of a surfactant, and 28-79 wt. % water.

14. The glove of claim 13, wherein the polymeric glove is a polyvinyl chloride glove.

15. The glove of claim 13, wherein the silicon dioxide comprises particles sized from 0.01 micron to 0.2 micron.

* * * * *